United States Patent [19]

Cannon

[11] Patent Number: 4,728,265

[45] Date of Patent: Mar. 1, 1988

[54] PERISTALTIC PUMP WITH CAM ACTION COMPENSATOR

[75] Inventor: Raymond Cannon, Poway, Calif.

[73] Assignee: Fisher Scientific Group Inc., San Diego, Calif.

[21] Appl. No.: 17,846

[22] Filed: Feb. 24, 1987

Related U.S. Application Data

[63] Continuation-in-part of Ser. No. 9,265, Jan. 30, 1987.

[51] Int. Cl.[4] .......................... F04B 43/12; E05D 1/00
[52] U.S. Cl. .................................. 417/363; 417/474; 16/225; 16/226
[58] Field of Search ........................ 417/474–477, 417/363; 16/225, 226

[56] References Cited

U.S. PATENT DOCUMENTS

| | | | |
|---|---|---|---|
| 1,055,516 | 3/1913 | Carter | 16/226 |
| 2,483,304 | 9/1949 | Vogel | 16/226 |
| 3,137,242 | 6/1964 | Hahn | 103/152 |
| 3,140,666 | 7/1964 | Currie | 103/149 |
| 3,582,234 | 6/1971 | Isreeli et al. | 417/53 |
| 3,737,251 | 6/1973 | Berman | 417/12 |
| 4,095,923 | 6/1978 | Cullis | 417/475 |
| 4,155,362 | 5/1979 | Jess | 128/214 |
| 4,233,001 | 11/1980 | Schmid | 417/475 |
| 4,278,085 | 7/1981 | Shim | 128/214 |
| 4,373,525 | 2/1983 | Kobayashi | 128/214 |
| 4,403,712 | 9/1983 | Wiesinger | 16/225 |
| 4,414,705 | 11/1983 | Ostrowsky | 16/225 |
| 4,479,797 | 10/1984 | Kobayashi | 604/153 |
| 4,482,347 | 11/1984 | Borsanyi | 604/153 |
| 4,559,038 | 12/1985 | Berg et al. | 604/153 |
| 4,653,987 | 3/1987 | Tsuji et al. | 417/412 X |

FOREIGN PATENT DOCUMENTS

60-230582  11/1985  Japan .................... 417/477

Primary Examiner—Carlton R. Croyle
Assistant Examiner—Theodore Olds
Attorney, Agent, or Firm—Workman, Nydegger & Jensen

[57] ABSTRACT

A linear peristaltic device for pumping medical solutions to a patient comprises a hinged pivot or hinged attachment between the peristaltic drive mechanism and its associated platen. An IV tube, through which the medical solutions are to be pumped is received and held between the peristaltic drive mechanism and the platen during operation of the device. The device also includes a compliant means which normally urges the peristaltic mechanism toward the platen but which yields, as necessary, to limit the force the peristaltic mechanism can exert against the tube.

30 Claims, 9 Drawing Figures

PERISTALTIC PUMP WITH CAM ACTION COMPENSATOR

BACKGROUND

This is a continuation in part of U.S. patent application Ser. No. 009,265, filed Jan. 30, 1987.

The present invention relates generally to peristaltic pumps which are used to pump fluids through resilient tubes. More particularly, the present invention relates to the drive mechanism of a linear peristaltic pump and to the arrangement for a mechanical compensator which minimizes the force that can be exerted by the peristaltic mechanism against the tube. The present invention is particularly, but not exclusively, useful in the health care field for the intravenous administration of medical solutions to patients.

DESCRIPTION OF THE PRIOR ART

Various devices have been proposed which are specifically and uniquely designed for the intravenous (IV) infusion of medical solutions to patients. Without exception, the objective in each instance is to provide a device which can reliably and accurately control the flow of fluid to the patient. Typically, such devices are classified either as pumps or controllers. The difference between the two being that a controller uses the effect of gravity to infuse fluids to a patient while pumps generate a mechanical pressure on the fluid for this purpose. The present invention is concerned with pumps.

After having distinguished pumps from controllers, pumps can be further divided into categories depending on how the particular pump exerts pressure on the infused fluid. Of the many types of pumps used for IV therapy, the present invention is concerned with that type which exerts a peristaltic action on the tube through which the fluid is being pumped. More specifically, the present invention is concerned with pumps which fall generally into the category of linear peristaltic pumps.

Although the actual design for a linear peristaltic pump will differ from pump to pump, all such pumps require the mechanical interaction of the following basic elements: a platen; a resilient tube through which fluid is to be pumped; a peristaltic means (i.e. structure capable of creating a moving zone of occlusion along the tube); and a drive mechanism for the peristaltic means. For its operation, the linear peristaltic pump must cause these elements to cooperate in a precise manner. Specifically, the peristaltic means must operatively engage with the IV tubing through which the medical solutions are to be pumped. As is well known by the skilled artesan, this engagement requires placement of the tube between the platen and the peristaltic means.

It should be apparent that for a moving zone of occlusion to be generated along the tube, the pump must squeeze the tube in some sequential manner. This squeezing action occurs as the result of relative movement between the platen and the peristaltic means and this, in turn, generates forces between the components of the pump. Unless the device has properly engineered tolerances which are designed to relieve these forces, the squeezing action can result in a seizure or stoppage of the device. Obviously, such an occurrence is to be avoided. On the other hand, the pump must be able to exert sufficient forces on the tube to create the zone of occlusion. Consequently, there is a limited range of forces which are acceptable for proper operation of the pump.

In addition to causing an actual seizure or stoppage of the pump, forces generated during pump operation can also create problems with the tube itself. Specifically, even though the pump may continue to operate, excessive occlusion or pinching forces on the tube can cause both short-term and long-term deformations of the tube that will result in uncontrolled variations in fluid flow through the tube. Also, excessive occlusion forces can cause spalling of the tube with the potentially catastrophic infusion of particles to the patient. Admittedly, some of the above stated problems can be alleviated by the selection of proper tubing materials. Even proper tube selection, however, does not completely eliminate the problem.

As impliedly stated above, the mechanical problems with peristaltic pumps stem from the close tolerances required between its interactive parts for proper operation. These problems are particularly pronounced since tolerances tend to back up into the movement. Thus, each pump will react and behave differently to the same problem.

In order to visualize the nature of these problems, first consider the sequence in which the interactive parts cooperate. Starting at one end of the combination, there is the platen. Then, in sequential order, there is the tube, the peristaltic means and the drive mechanism. To prevent seizure of the mechanism, one or more of these elements must yield whenever an excessive force is generated. Once a particular tube is selected, specific predetermined dimensional limitations are introduced into the combination. Thus, the tube itself cannot be expected to provide the necessary resilience to obviate the problem. Indeed, rather than absorb the excess forces with tube resiliency, the effort is more properly focused on ways that limit the force exerted on the tube. Consequently, design efforts have focused on the other elements in the device.

One way in which excessive forces in the peristaltic pump can be alleviated is to allow the platen to yield. For example, U.S. Pat. No. 4,373,525 to Koboyashi discloses a linear peristaltic pump having a spring loaded platen. The same purpose is accomplished, but with dissimilar structure, by the device of U.S. Pat. No. 4,482,347 to Borsanyi which discloses a resilient surface set into the face of the platen. Both designs, however, have certain disadvantages.

First, consider the design incorporating a platen with a resilient surface. Such a design generally operates with a distance between the peristaltic mechanism and the platen that varies according to the resiliency of the platen without regard for the wall thickness of the tube. Thus, it happens that the dimensional requirements to occlude a thin walled tube can create problems when thicker walled tubes are used. Indeed, for a thicker walled tube, not only is greater force exerted on the tubing but the portion of the tube that is occluded will be increased. The greater force, of course, adds trauma to the tube and the increased occlusion area reduces the fluid volumetric flow. Both effects are unwanted.

Second, in the case of a spring-loaded or "floating" platen it can be demonstrated that conventional designs of this type generate a varying force at the point of tube occlusion. This is dependent on where the occlusion occurs. To illustrate this point, consider a platen supported at either end by a spring which exerts a force F against the platen. When the occlusion occurs over a support point, the reactive force of the peristaltic mechanism against the tube will equal F. On the other hand, when the occlusion occurs at mid span, the reactive force of the peristaltic mechanism against the tube will equal 2F. This unwanted variation in force on the tube can create some of the problems previously discussed.

Excessive forces within the peristaltic pump can also be alleviated by allowing the peristaltic mechanism to yield. If this is done, the dimensional relationship between the drive mechanism for the peristaltic means and the platen can be fixed. Within this fixed relationship the design compensates for variations in tubing dimensions by making the peristaltic mechanism complaint. Examples of such mechanisms include the device disclosed in U.S. Pat. No. 3,137,242 to Hahn in which tension springs are used to engage the peristaltic rollers with the tube. Another example of a yielding or complaint peristaltic mechanism is found in U.S. Pat. No. 4,095,923 to Cullis which teaches the use of yieldable rubber bushings between peristaltic rollers and the driving axles. Still another example of such a means is the design for a linear peristaltic pump in which individually resilient fingers are operatively associated with a rotating cam shaft. The shortcoming for these designs, however, is that each resilient structure introduces its own variable into the operation of the device.

The foregoing discussion leads to a consideration of the possibility that two components, rather than one, should be allowed to yield. For reasons previously stated, the tube itself will be eliminated from this consideration. Also, it is to be understood that the cyclical movement of the means causing the peristaltic action is not a yielding movement which will alleviate an excessive force on the tube. This leaves the platen, the entire peristaltic means and the drive motor for consideration. First, consider the possibility of allowing both the platen and the peristaltic means to yield. Since the tube is between these elements, they must yield independently of each other. Not only is this a complex mechanical arrangement, it can be very difficult to manufacture and even more difficult to properly engineer for predictable and reliable fluid flow. Further, the interaction of so many independent variables makes linearization of the flow very hard, if not impossible, to accomplish. On the other hand, if the entire peristaltic means and its associated drive mechanism are combined and allowed to yield together relative to the platen, the only variable which must be controlled is the amount of force exerted by the peristaltic mechanism against the tube. The present invention recognizes that such an arrangement can be constructed and done in a manner which allows the combination to yield against the opposing effect of a simple spring force.

In light of the above, the present invention addresses the many problems associated with linear peristaltic pumps which are created by an inability to constrain the forces exerted on the tube within an efficient range for a proper pumping operation. Further, the present invention recognizes that engineering tolerances can be critical for a peristaltic pump and that the difficulty in manufacturability increases proportionately with this criticality.

Accordingly, it is an object of the present invention to provide a peristaltic pumping device which minimizes trauma to the tube during the pumping operation. Ancillary to this are the objectives of providing a peristaltic pump which reduces the risk of spalling the tube and which extends the useful life of the tube. Another objective of the present invention is to reduce fluid volumetric flow errors which result when variations in tubing wall thickness affect the size of the occlusion zone. Still another object of the present invention is to reduce power and consequently, torque requirements. Yet another objective of the present invention is to provide a linear peristaltic pump which is easy to manufacture and which does not require extremely close tolerances between its mechanical components for proper assembly. Another objective of the present invention is to provide a durable and reliable peristaltic pump which is cost effective and which accurately infuses fluids to patients.

SUMMARY OF THE INVENTION

The preferred embodiment of the linear peristaltic hinged cam action compensator of the present invention comprises structure which provides for a yielding or compliant movement between the platen and the drive mechanism. More specifically the preferred embodiment of the present invention comprises a casing on which a rotatable shaft is mounted which has a plurality of cams spaced therealong in a helical arrangement. Operatively associated with each cam is a peristaltic finger. A housing is hingedly attached to the casing with the transverse axis of the hinge aligned substantially parallel to the longitudinal axis of the cam shaft. The housing itself is formed as a rectangular box having no top or bottom. A series of grooves formed on the inner surface of its sides are established for respectively receiving the peristaltic fingers. In its combination with the casing, the housing serves as a guide for the peristaltic fingers and constrains them for reciprocal linear movement in accordance with the action of the cam shaft on the fingers. A compliant means, such as a spring, is attached between the casing and the housing to urge rotation of the casing about the hinge axis toward the housing in a manner which holds the peristaltic fingers in the grooved guides of the housing. Contrarily, the compliant means tends against a rotation of the casing about the hinge axis which would lift the fingers out of the housing. The present invention further comprises a platen which can be positioned into a fixed spacial relationship with respect to the housing to hold a resilient tube between the platen and the peristaltic fingers during a rotation of the shaft for a pumping operation.

In another embodiment of the present invention, the connection between the housing and the casing is accomplished by an integral hinge formed at their juncture to establish a pivotal movement therebetween. In still another embodiment of the present invention the connection between the casing and the housing can be accomplished by joining them together with a flexure which obviates the need for a compliant or resistive means.

The novel features of this invention as well as the invention itself both as to its organization and operation will be best understood from the accompanying drawings taken in conjunction with the accompanying description in which similar reference characters refer to similar parts and in which:

DESCRIPTION OF THE PREFERRED EMBODIMENT

Figure 1:
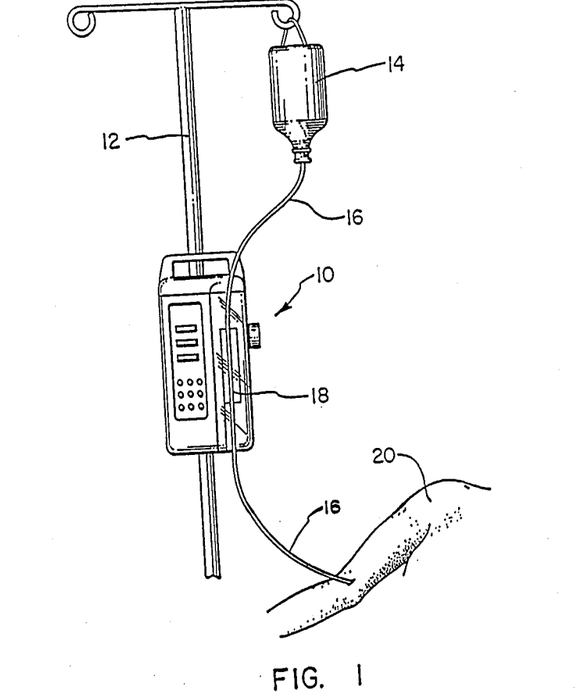
FIG. 1 is a front elevational view of a linear peristaltic pump incorporating the present invention shown in its working environment.

Referring initially to FIG. 1, a set up of the present invention is shown in its intended environment. In FIG. 1 a linear peristaltic pump generally designated 10 is shown mounted onto an IV pole 12. A fluid source 14 is hung from IV pole 12 in a manner well known in the art. IV tube 16 is connected into fluid communication with the fluid source 14 and operatively engaged with the pumping mechanism 18 of linear peristaltic pump 10. It is further shown in FIG. 1 that IV tube 16 entends from linear peristaltic pump 10 and is attached to patient 20. Thus, as shown in FIG. 1, it is intended that a linear peristaltic pump 10 operatively engaged with an IV tube 16 to a pump fluid from a fluid source 14 through the IV tube 16 to a patient 20. Pumping mechanism 18 of linear peristaltic pump 10 is shown by itself and separated from linear peristaltic pump 10 in FIG. 2.

Figure 2:
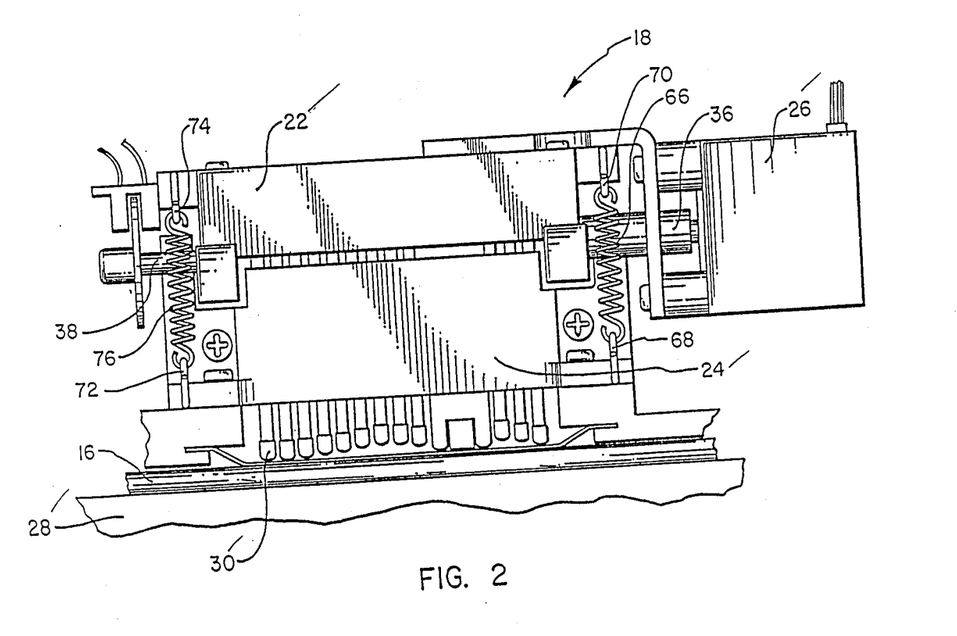
FIG. 2 is a side elevational view of the pumping mechanism of the present invention.

With reference to FIG. 2, the general arrangement of the major components of the pumping mechanism 18 and their interaction can been seen. Specifically, it is shown that pumping mechanism 18 includes a casing 22, a housing 24, and a drive motor 26, all of which are placed in operative association with a platen 28. The actual specifics of the cooperation of the structure of these components will be set forth in detail below. For the moment it suffices that drive motor 26 is operatively associated with casing 22 for moving peristaltic fingers 30 against IV tube 16 which is supported by platen 28.

As is well known in the pertinent art, the action of peristaltic fingers 30 against IV tube 16 while tube 16 is being held between peristaltic fingers 30 and the platen 28 creates a moving zone of occlusion along tube 16 which effectively pumps fluid through tube 16 to patient 20. A more detailed description of the components of pumping mechanism 18 of linear peristaltic pump 10 is best seen with reference to FIG. 3.

Figure 3:
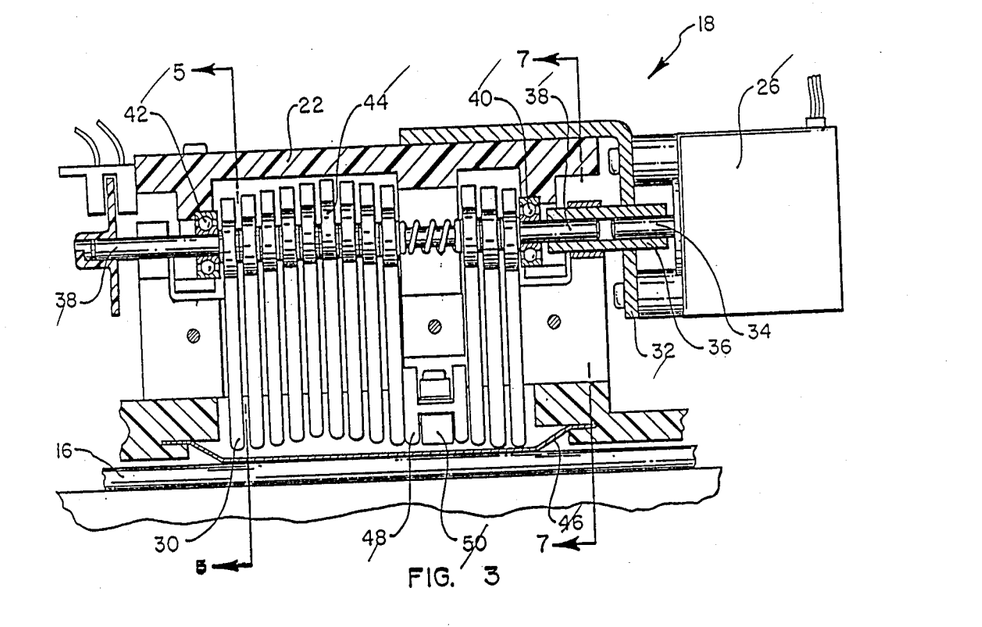
FIG. 3 is a side cross-sectional view along the centerline of the pumping mechanism of the present invention which corresponds to the view seen in FIG. 2.

In FIG. 3 it can be seen that drive motor 26 is attached to a bracket 32. As shown, this attachment is accomplished through the use of screws, but it will be appreciated by those skilled in the art that this attachment can be accomplished by any number of ways so long as the attachment establishes a fixed relationship between the drive motor 26 and bracket 32. Drive motor 26 is operatively connected with a drive shaft 34 to cause rotation of drive shaft 34. A sleeve 36 connects drive shaft 34 with cam shaft 38 so that the rotational motion of drive shaft 34 is transferred through sleeve 36 to cam shaft 38. Casing 22 includes a bearing 40 and a bearing 42 which support cam shaft 38 for rotation relative to casing 22 and bracket 32 is fixedly attached to casing 22 in a manner which holds drive motor 26, cam shaft 38 and casing 22 in the relationship shown in FIG. 3. Thus, it will be appreciated that cam shaft 38 remains in the same position with respect to casing 22 and that the rotation of cam shaft 38 about its longitudinal axis can be accomplished without changing this relationship.

Also seen in FIG. 3, arranged along the length of cam shaft 38, are a series of cams 44. As will be appreciated by the skilled artesan, cams 44 are arranged lengthwise along cam shaft 38 in a helical relationship. This arrangement of the cams 44 along cam shaft 38, when operatively associated with peristaltic fingers 30, cause a sequential reciprocal motion of the peristaltic fingers 30 that results in a peristaltic action of the fingers 30 against IV tube 16.

Also shown in FIG. 3 is a membrane 46 which separates the peristaltic fingers 30 from the IV tube 16. Incorporation of membrane 46 serves as a barrier to prevent the unwanted entry of fluids from the IV tube 16 or fluid source 14 into the internal working elements of pumping mechanism 18. Further, as seen in FIG. 3, pumping mechanism 18 of the present invention is shown incorporating stationary members 48 and a pressure sensor 50. The inclusion of these elements into pumping mechanism 18 are informational to show that the present invention is compatible with the dual mode infusion devices set forth in U.S. Pat. No. 4,617,014 and U.S. patent application Ser. No. 844,414 both of which are assigned to the same assignee as the present invention.

Figure 4:
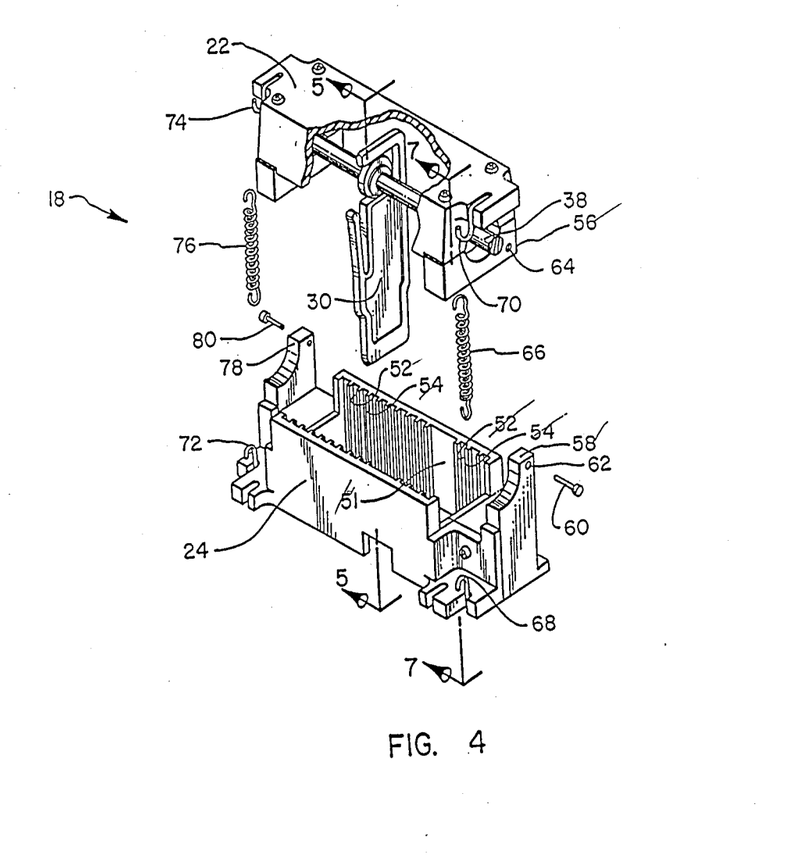
FIG. 4 is an exploded perspective view of the pumping mechanism with portions cut away for clarity.

The cooperation of structure between casing 22 and housing 24 is perhaps best seen with reference to FIG. 4. In the exploded view of pumping mechanism 18 shown in FIG. 4, it is perhaps more apparent that cam shaft 38 has a set relationship with casing 22 for rotation about its longitudinal axis. Also, it is seen in FIG. 4 that housing 24 is essentially a retangular shaped structure having an open top and an open bottom. The open bottom of housing 24 provides for the extension of peristaltic fingers 30 therethrough and the consequent operative engagement of peristaltic fingers 30 with IV tube 16. The interior side walls 51 of housing 24 are formed with a series of grooves 52 which are arranged in side by side relationship and separated by guides 54. The grooves 52 are established for receiving the peristaltic fingers 30 therein and guides 54 are intended to maintain peristaltic fingers 30 within grooves 54 for linear reciprocal action therein. The exact purpose of this will become clear as the discussion of the present invention proceeds.

The attachment of casing 22 to housing 24 is accomplished by a hinged relationship. To accomplish this connection casing 22 is formed with hinge ear 56 which can be positioned next to hinge tab 58 on housing 24. A hinge pin 60 inserted into hole 62 of hinge tab 58 and extending therethrough and into hole 64 of hinge ear 56 establishes the hinged relationship between casing 22 and housing 24. A second hinge point can also be established. More specifically FIG. 4 shows a hinge tab 78 and hinge pin 80 which can be attached to a hinge ear (not shown) on casing 22 in a manner similarly to that discussed for the attachment of hinge ear 56 with hinge tab 58. It will be understood by a person of ordinary skill in the art, that the hinge mechanism as shown for the present invention in FIG. 4 is only illustrative and that any arrangement whereby a hinged action is established between casing 22 and housing 24 will suffice for the present invention. Further, while one hinge point may be sufficient for operation of the present invention, a plurality of hinge points as disclosed herein are also appropriate.

Figure 8:
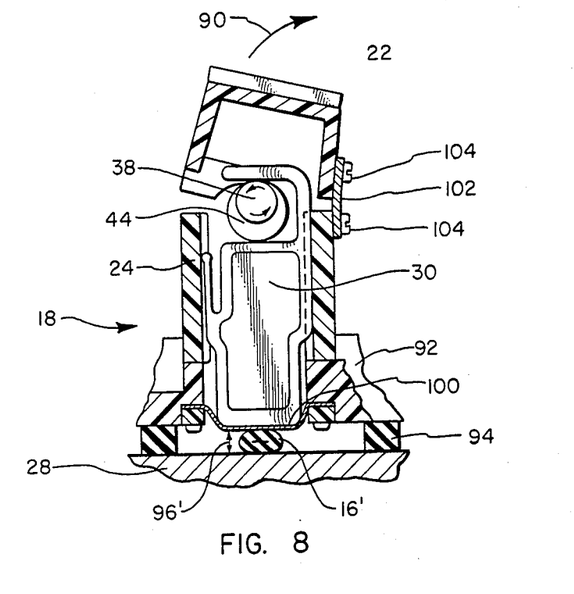
FIG. 8 is a cross-sectional view of the pumping mechanism for the embodiment comprising a flexure as seen along the line 5—5 in FIGS. 3 and 4.

In another embodiment of the present invention, casing 22 is pivotally connected with housing 24 by a flexure 102 as seen in FIG. 8. More specifically, flexure 102 is joined with casing 22 in a rigid manner by any means well known in the art such as by an anchor means 104. Flexure 102 is also fixedly joined with housing 24 by similar means. It is to be understood that the material which comprises flexure 102 can be selected in accordance with the bending requirements between the casing 22 and housing 24. Stated differently, flexure 102 can be selected with a desired stiffness or spring constant to suit the purposes of the present invention. As will be readily understood by the skilled artesan, such a flexure 102 at the juncture of casing 22 and housing 24 creates a pivot axis around which relative rotational motion between the casing 22 and housing 24 can be accomplished. Further, when a flexure 102 is used for purposes of joining casing 22 with housing 24 it is to be understood that the resilient means for resisting rotation of casing 22 relative to housing 24 is no longer required. Specifically, because of the stiffness inherent in the flexure 102, spring 66 and spring 76 can be eliminated from the structure of the pump 10. In all important respects, the operation of pump 10, when a flexure 102 is incorporated into its structure, is the same as for the perferred embodiment incorporating the hinged attachment of casing 22 to housing 24. The actual interworking of these components of structure remain unchanged.

Figure 9:
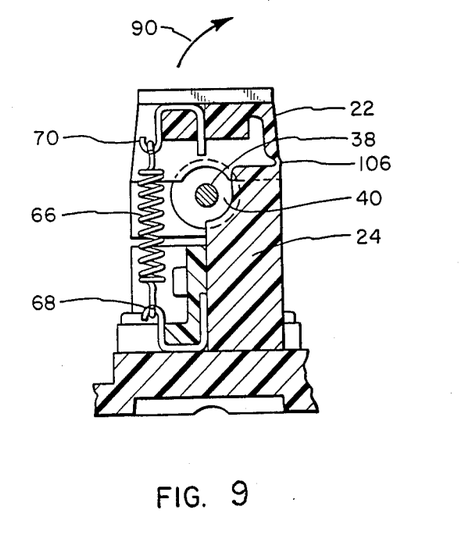
FIG. 9 is a cross-sectional view of the pumping mechanism comprising an integral hinge as seen along the line 7—7 in FIGS. 3 and 4.

FIG. 9, shows still another embodiment of the present invention for pump 10 wherein the connection between casing 22 and housing 24 is accomplished by an integral hinge 106. Integral hinge 106 is sometimes referred to by skilled artesans as a "living hinge". More specifically, integral hinge 106 comprises a section of reduced cross-sectional area to allow a rotational movement of casing 22 with respect to housing 24. As will be understood by the person of ordinary skill in the pertinent art, the incorporation of an integral hinge 106 allows casing 22, housing 24 and the integral hinge 106 to be manufactured by an injection molding procedure. Further, it will be understood by the person of ordinary skill in the pertinent art that with the particular embodiment incorporating an integral hinge 106, the spring 66 as disclosed elsewhere for the present invention needs to be incorporated. In all important respects, the pump 10 which incorporates an integral hinge 106 for connecting casing 22 with housing 24 functions in an identical manner as disclosed for the preferred embodiment of the present invention.

To further show the cooperation of casing 22 in its relationship with housing 24 reference is still made to FIG. 4. There can be seen that in addition to the hinged relationship between casing 22 and housing 24 previously discussed, a spring 66 urges casing 22 toward housing 24 in a predictable manner. To do this, spring 66 is attached to housing 24 at an attachment point 68 and further attached to casing 22 at an attachment point 70. It is understood that the attachment of spring 66 between housing 24 and casing 22 can be accomplished by any manner well known in the art and, that spring 66 is only illustrative of the various flexible structures which could accomplish the same purpose for the present invention.

The interworking of the hinged attachment of casing 22 to housing 24 and the counteracting spring attachment therebetween is further seen by reference back to FIG. 2 wherein spring 6 is shown as the attachment between casing 22 and housing 24 by its respective connections with attachment point 70 and attachment point 68. It is also shown in FIG. 2 that a second spring 76 is attached to housing 24 and casing 22 respectively at attachment points 72 and 74.

Recall that casing 22 is hingedly attached to housing 24 for rotation about a transverse axis which is defined and established by the hinged connections between casing 22 and housing 24 at hinge tabs 58 and 78. Also, recognize that the rotation of casing 22 relative to housing 24 about the transverse action of the hinge is constrained by the attachment of springs 76 and 66 bring casing 22 into contact with housing 24 in a manner that maintains the positioning of peristaltic fingers 30 within the respective grooves 52 of housing 24.

Figure 5:
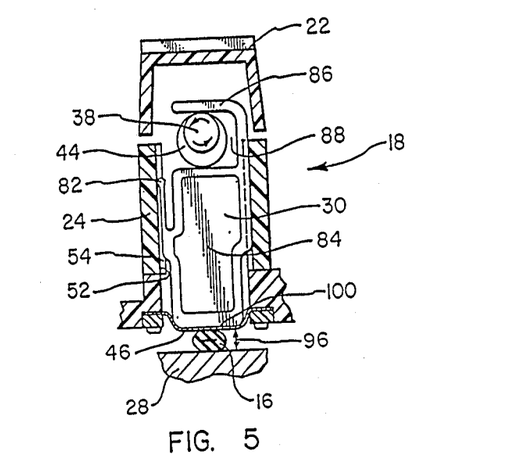
FIG. 5 is a cross-sectional view of the pumping mechanism as seen along the line 5—5 in FIGS. 3 and 4.

As shown in FIGS. 4 and 5, peristaltic finger 30 is positioned within housing 24 for reciprocal movement along the grooves 52 established by guides 54. The body 84 of peristaltic finger 30 is formed with a resilient arm 82 that rests within the groove 52 to stabilize the lateral movement of peristaltic finger 30 within housing 24 without creating an interference between peristaltic finger 30 and housing 24. Also, in FIG. 5 it is seen that peristaltic finger 30 is formed with an extender 86 to establish a recess 88 within which a cam 44 may be received. With this engagement, finger 30 moves linearly and reciprocally within housing 24 dependent upon the urging of cam 44 against extender 86 and body 84 of peristaltic finger 30. Although the particular cross-sectional view of pumping mechanism 18 as seen in FIG. 5 does not show the attachment of housing 24 with respect to platen 28, it is to be understood that the platen 28 is brought into a fixed dimensional relationship with respect to housing 24 during the operation of linear peristaltic pump 10. For any particular peristaltic pump 10 it is only important that some mechanism allows for such a fixed relationship between platen 28 and pumping mechanism 18. As suggested in FIG. 6 this can be done through an actual fixed attachment between housing 24 and platen 28 such as the use of connector 92 and attachment 94. It is within the spirit of the present invention to recognize that IV tube 16 needs only to be placed for operative engagement between peristaltic fingers 30 and platen 28. Thus, so long as the relationship between housing 24 and platen 28 can remain fixed, while relative motion with respect to platen 28 is accomplished by other components of pumping mechanism 18, the purposes of the present invention can be accomplished.

Reference is now made to FIG. 7 to again appreciate that casing 22 is hingedly mounted to the housing 24 for rotation about a hinge pin 60. As will be appreciated by the skilled artesan, hinge pin 60 establishes the transverse axis for the hinged connection between casing 22 and housing 24. Further, as previously discussed, spring 66 resists rotation of casing 22 about housing 24 in the direction indicated by arrow 90. With this cooperation of structure in mind, reference is directed back to FIGS. 5 and 6 wherein it can be seen that peristaltic finger 30 is mounted in housing 24 for reciprocal motion in respect thereto.

The motion of peristaltic finger 30 with respect to housing 24 is accomplished in either or both of two ways. First, the rotation of cam shaft 38 by drive motor 26 urges cams 44 against peristaltic finger 30 to create a linear reciprocal movement of peristaltic fingers 30. The second manner in which peristaltic fingers 30 can be moved relative to housing 24 is in response to the movement of casing 22 with respect to housing 24. Recall that cam shaft 38 is mounted onto casing 22. Thus, any force which causes a displacement of cam shaft 38 will also manifest itself as a movement of casing 22. Since casing 22 is constrained to rotate about the axis 98 established by hinge 60, this movement will be opposed by the action of springs 66 and 76.

In order to appreciate the mechanism by which the present invention brings force on the IV tube 16 to create a moving zone occlusion therealong, consider an IV tube 16 having a specific wall thickness which creates a dimension between platen 28 and peristaltic 30 equivalent to dimensional indicator 96 shown in FIG. 5. In accordance with the present invention, when platen 28 is fixed relative to housing 24, dimension 96 will be determined only by the action of peristaltic finger 30 against IV tube 16. Thus in a static condition of occlusion, the force that peristaltic finger 30 exterts against IV tube 16 will be a function of the dimension 96.

Figure 6:
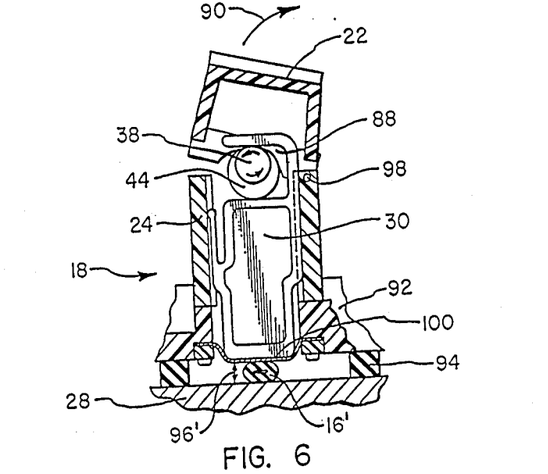
FIG. 6 is cross-sectional view of the pumping mechanism as seen in FIG. 5 when the mechanism is compensating for an excessively thick walled tube.
Figure 7:
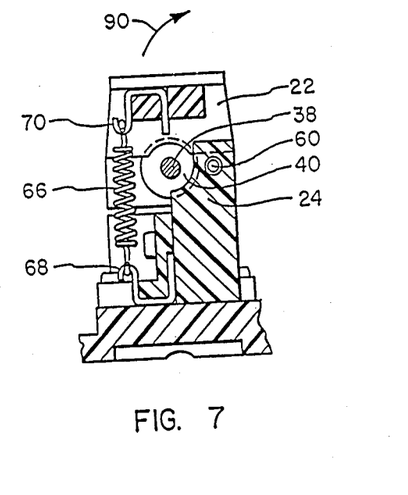
FIG. 7 is a cross-sectional view of the pumping mechanism as seen along the line 7—7 in FIGS. 3 and 4.

The importance of the dimensional interaction of pumping mechanism 18 with platen 28 is now best appreciated by cross referencing FIG. 5 with FIG. 6.

As previously indicated, housing 24 is established in fixed spatial relationship with respect to platen 28. When IV tube 16 is supported by platen 28 for operative engagement with pumping mechanism 18, the distance 96 between edge 100 of peristaltic finger 30 and platen 28 will be, in part, determined by the characteristics of IV tube 16. During operation, sufficient force needs to be exterted by the peristaltic finger 30 against IV tube 16 to cause a periodic occlusion. However, it is necessary to constrain or limit this force so that the adverse effects of an excessive force against IV tube 16 are eliminated. In FIG. 5 it can be seen that any relief from the action of peristaltic finger 30 against IV tube 16 will be manifested through peristaltic finger 30 to cam 44 on cam shaft 38. Recall that cam shaft 38 is mounted for rotation on casing 22. Therefore, any movement of cam shaft 38 caused by a backforce exerted from peristaltic 30 will be transmitted to the casing 22 and, as discussed earlier with respect to FIG. 7, will result in a rotation of casing 22 about hinge axis 98 relative to the housing 24. The resistance to such a rotation of casing 22 is caused by springs 66 and 76. Therefore the resistive force encountered by the mechanism can be established through proper selection of springs 66 and 76.

FIG. 6 shows an IV tube 16' having thicker walls than IV tube 16 in FIG. 5. This will correspondingly cause a change in the distance 96 to 96'. As will be appreciated by the skilled aretsan, this dimensional change manifests itself as a force through peristaltic finger 30 against cam shaft 38. This, in turn, causes cam shaft 38 and casing 22 to rotate about hinge axis 98. During such a rotation, it will be appreciated that the relationship of cam shaft 38 with respect to casing 22 remains unchanged. Thus, pump 10 will operate equally well regardless whether cam shaft 38 and casing 22 are oriented as shown in FIG. 5 or as shown in FIG. 6. Consequently, the actual pumping operation of the linear peristaltic pump 10 of the present invention is accomplished independently of the wall thickness of tube 16.

OPERATION

In the operation of pump 10, IV tube 16 is positioned between platen 28 and pumping mechanism 18. Cam shaft 38 is mounted on casing 22 and drive motor 26 is operatively connected to cam shaft 38 to cause its rotation. The consequent action of cams 44 on cam shaft 38 causes a linear reciprocal movement of the peristaltic fingers 30 within grooves 52 of housing 24. This movement manifests itself as a moving zone of occlusion against IV tube 16.

The forces created by peristaltic fingers 30 against IV tube 16 are limited by the interaction of casing 22 with housing 24. Specifically, and regardless of the dimensions of IV tube 16 being used in association with linear peristaltic pump 10, the peristaltic fingers 30 are able to move into contact with IV tube 16 only to the point that any further force exerted against a peristaltic finger 30 will cause a movement between casing 22 and housing 24.

More specifically, any excessive backforce created on peristaltic fingers 30 by variations in the dimensions of IV tube 16 will be exerted against cam shaft 38 to rotate casing 22 about hinge axis 98 relative to housing 24. Resistance to this rotational motion of casing 22 about hinge axis 98 is caused by the action of springs 66 and 76 and their connections between casing 22 and 24. Thus, it will be appreciated by the skilled artesan that the peristaltic action of pumping mechanism 18 against IV tube 16 can be accomplished independently of dimensional variables introduced by IV tube 16 and with equal efficiency for various IV tubes 16.

It is to be understood that the relative motion between casing 22 and housing 24 about hinge axis 98 can be accomplished by various structures. Specifically, as disclosed herein for the preferred embodiment, a hinge can be used. Alternatively, a flexure 102 may be used to connect casing 22 with housing 24. In still another embodiment, an integral hinge 106 can be incorporated for this purpose.

While the particular cam action compensator as herein shown and disclosed in detail is fully capable of obtaining the objects and providing the advantages hereinbefore stated, it is to be understood that it is merely illustrative of the presently preferred embodiment of the invention and that no limitations are intended to the details of construction or design herein shown other than as defined in the appended claims.

I claim:
1. An apparatus for pumping fluids through a tube which comprises:
   a base for supporting said tube in a substantially linear orientation;
   means for generating a peristaltic action on said tube; and
   a flexure connecting said base with said peristaltic means for pivotal movement of said peristaltic means between a first position and a second position about an axis substantially parallel to the longitudinal axis of said tube, said flexure biased to yieldably urge said peristaltic means toward said first position and against said base for operative engagement of said peristaltic means with said tube.

2. An apparatus as recited in claim 1 wherein said peristaltic means comprises:
   a cam shaft having a plurality of cams spaced in a helical relationship therealong; and
   a plurality of fingers operatively connected with said cams.

3. An apparatus as recited in claim 2 further comprising a casing for operatively mounting said cam shaft thereon.

4. An apparatus as recited in claim 3 further comprising a housing fixedly associated with said base, said housing having a plurality of grooves for receiving said fingers therein to constrain said fingers for linear reciprocal movement.

5. An apparatus as recited in claim 4 wherein said base comprises a platen.

6. A linear peristaltic pump for pumping fluids through an IV tube having a cam action compensator which comprises:
   a platen mounted on said pump;
   a housing fixedly attached to said pump to receive said tube between said housing and said platen;
   a plurality of fingers slidably mounted on said housing to squeeze said tube between said fingers and said platen to create a moving zone of occlusion along said tube;
   a cam shaft operatively coupled to said fingers;
   a casing having said cam shaft rotatably mounted thereon; and
   a flexure connecting said casing to said housing for rotation of said casing between a first position and a second position about an axis substantially parallel to the longitudinal axis of said tube and for urging said casing toward said first position to compensate for the action between said fingers and said platen.

7. A peristaltic pump as recited in claim 6 wherein said cam shaft has a plurality of cams mounted in a helical relationship therealong.

8. A peristaltic pump as recited in claim 7 wherein said fingers are formed with resilient arms to compensate for rotational motion of said fingers within said housing.

9. A peristaltic pump as recited in claim 8 further comprising a motor operatively connected with said cam shaft.

10. A linear peristaltic cam action compensator which comprises:
    a casing;
    a rotatable cam shaft operatively mounted on said casing;
    a plurality of fingers coupled to said cam shaft;
    a flexure; and
    a housing for operatively receiving said fingers, said housing yieldably connected to said casing by said flexure to establish a pivot axis substantially parallel to the longitudinal axis of said cam shaft for movement of said casing between a first position and a second position and for urging said casing toward said first position to resist movement of said casing about said axis.

11. A compensator as recited in claim 10 further comprising a resilient tube; and a platen operatively associated with said housing to hold said tube therebetween.

12. A compensator as recited in claim 11 wherein said fingers are formed with resilient arms to ensure linear movement of said fingers relative to said housing.

13. An apparatus for pumping fluids through a tube which comprises:
    a base for supporting said tube in a substantially linear orientation;
    means for generating a moving zone of occlusion along said tube;
    an integral hinge formed at a juncture between said base and said generating means for pivoting of said generating means between a first position and a second position about an axis substantially parallel to the longitudinal axis of said tube; and
    resisting means biased to yieldably urge said generating means toward said first position and against said base for operative engagement of said generating means with said tube.

14. An apparatus as recited in claim 13 wherein said peristaltic means comprises:
    a cam shaft having a plurality of cams spaced in a helical relationship therealong; and
    a plurality of fingers operatively connected with said cams.

15. An apparatus as recited in claim 14 further comprising a casing for operatively mounting said cam shaft thereon.

16. An apparatus as recited in claim 3 further comprising a housing fixedly associated with said base, said housing having a plurality of grooves for receiving said fingers therein to constrain said fingers for linear reciprocal movement.

17. An apparatus as recited in claim 16 wherein said resisting means is a spring connected between said casing and said housing.

18. An apparatus as recited in claim 17 wherein said integral hinge is positioned with its transverse axis substantially parallel to the longitudinal axis of said cam shaft.

19. An apparatus as recited in claim 18 wherein said case comprises a platen.

20. A linear peristaltic pump for pumping fluids through an IV tube having a cam action compensator which comprises:
    a platen mounted on said pump;
    a housing fixedly attached to said pump to receive said tube between said housing and said platen;
    a plurality of fingers slidably mounted on said housing to squeeze said tube between said fingers and said platen to create a moving zone of occlusion along said tube;
    a cam shaft operatively coupled to said fingers;
    a casing having said cam shaft rotatably mounted thereon;
    an integral hinge connecting said casing to said housing, said hinge establishing an axis of rotation for said casing substantially parallel to the longitudinal axis of said cam shaft for movement of said casing between a first position and a second position; and
    resisting means biased to yieldably urge said casing toward said first position and onto said housing to compensate for the action between said fingers and said platen.

21. A peristaltic pump as recited in claim 20 wherein said cam shaft has a plurality of cams mounted in a helical relationship therealong.

22. A peristaltic pump as recited in claim 21 wherein said resisting means is a spring.

23. A peristaltic pump as recited in claim 22 wherein said fingers are formed with resilient arms to compensate for rotational motion of said fingers within said housing.

24. A peristaltic pump as recited in claim 23 further comprising a motor operatively connected with said cam shaft.

25. A linear peristaltic cam action compensator which comprises:

a casing;

a rotatable cam shaft operatively mounted on said casing;

a plurality of fingers coupled to said cam shaft;

a housing for establishing linear reciprocal movement of said fingers in response to the rotation of said cam shaft;

an integral hinge pivotally connecting said casing to said housing, said hinge establishing an axis of rotation for said casing substantially parallel to the longitudinal axis of said cam shaft for movement of said casing between a first position and a second position; and means yieldably connecting said housing to said casing to bias said casing toward said first position and resist movement of said casing about the hinge axis.

26. A compensator as recited in claim 25 wherein said cam shaft further comprises cams operatively connected with said fingers for peristaltic movement of said fingers.

27. A compensator as recited in claim 10 further comprising a resilient tube; and a platen operatively associated with said housing to hold said tube therebetween.

28. A compensator as recited in claim 27 wherein said fingers are formed with resilient arms to ensure linear movement of said fingers relative to said housing.

29. A compensator as recited in claim 28 wherein said hinged connection is oriented with its transverse axis substantially parallel to the longitudinal axis of said cam shaft.

30. A compensator as recited in claim 29 wherein said resisting means is a spring.

* * * * *